United States Patent [19]

Duffett

[11] Patent Number: Plant 5,409

[45] Date of Patent: Feb. 26, 1985

[54] CHRYSANTHEMUM PLANT NAMED CHAMP

[75] Inventor: William E. Duffett, Salinas, Calif.

[73] Assignee: Yoder Brothers, Inc., Barberton, Ohio

[21] Appl. No.: 505,085

[22] Filed: Jun. 16, 1983

[51] Int. Cl.[3] ..... A01H 5/00
[52] U.S. Cl. ..... Plt./78
[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Champ having flat capitulum form; decorative capitulum type; golden yellow summer ray floret color; golden bronze winter ray floret color; diameter across face of capitulum ranging from 70 to 90 mm. at maturity; uniform nine week photoperiodic flowering response to short days; medium plant height and spreading branching pattern that adapts equally well to pinched disbud or spray pot mum programs.

3 Drawing Figures

1

The present invention comprises a new and distinct cultivar of *Chrysanthemum morifolium,* Ramat., named Champ.

Champ is a product of a planned breeding program which had the objective of creating new chrysanthemum cultivars for pinched disbud and spray pot mum programs having decorative capitulum type, yellow floret color, nine week flowering response and the ability to produce commercially acceptable quality in year round programs. Such traits in combination were not present or needed improvement in previously available commercial cultivars.

Champ was originated from a cross made in a controlled breeding program in Salinas, Calif. in 1979. The female parent was British Gold, disclosed in U.S. Plant Pat. No. 4,290, a bronze decorative commercial variety. The male parent of Champ was identified as 787951, an unnamed bronze decorative seedling originated from a cross between a seedling from Royal Purple (U.S. Plant Pat. No. 3,589) × Mandalay, and a seedling from Mandalay × Sunstar.

Champ was discovered and selected as one flowering plant within the progeny of the stated cross by William E. Duffett on February 1980 in a controlled environment in Salinas, Calif.

The first act of asexual reproduetion of Champ was accomplished when vegetative cuttings were taken from the initial selection in June 1980 in a controlled environment in Salinas, Calif. by a technician working under formulations established and supervised by William E. Duffett. Horticultural examination of selected units initiated Mar. 3, 1981 has demonstrated that the combination of characteristics as herein disclosed for Champ are firmly fixed and are retained through successive generations of asexual reproduction.

Champ has not been observed under all possible environmental conditions. The phenotype may vary significantly with variations in environment such as temperature, light intensity and day length. The observations, measurements and comparisons describe plants grown in Salinas, Calif. and Leamington, Canada under greenhouse conditions which approximate those generally used in commercial practice.

The following traits have been repeatedly observed and are determined to be basic characteristics of Champ

2 which in combination distinguish this chrysanthemum as a new and distinct cultivar:

(1) Flat capitulum form;

(2) Decorative capitulum type;

(3) Golden yellow summer ray floret color, golden bronze in winter;

(4) Diameter across face of capitulum ranging from 70 to 90 mm. at maturity;

(5) Uniform nine week photoperiodic flowering response to short days;

(6) Medium plant height requiring 2 long day weeks prior to pinch and short days, and 1-2 applications of 2500 ppm B-9 14 and 21 days after the beginning of short days to attain a flowered plant height of 25 to 35 cm.; and (7) Prolific, spreading branching pattern that adapts equally well to pinched disbud or spray pot mum programs.

The accompanying photographic drawings depict typical foliage and inflorescence characteristics of Champ. Sheet 1 is a color photograph of a plant of Champ grown as a pinched spray pot mum with center buds removed, with colors being as accurate as possible with renditions of this type. Sheet 2 is a black and white photograph of three views of the inflorescence of Champ. Sheet 3 shows the leaves of Champ in three stages of development (mature, intermediate, immature).

Of the many commercial cultivars known to the present inventor, the most similar in comparison to Champ is Yellow Mandalay, an unpatented but commercial cultivar. Reference is made to attached Chart A which compares certain characteristics of Champ to those same characteristics of Yellow Mandalay.

Under the reduced temperature of winter and fall flowering Champ expresses a golden bronze color; Yellow Mandalay becomes yellow tinged bronze. In the spring and summer Champ is a golden yellow; Yellow Mandalay is a clear yellow.

The two cultivars are similar in capitulum form, type and size. They are also similar in branching pattern and plant height.

Yellow Mandaly is less tolerant of high summer temperature (approximately 26° C.-32° C.), slowing in response to 11 weeks. Champ normally responds as a late 9 in the same period.

Spray pots receiving center bud removal show Champ's advantage over Yellow Mandalay of more rapid and uniform lateral bud development.

In the following description, color references are made to The Royal Horticultural Society Colour Chart. The color values were determined between 9:45 and 10:15 A.M. on Aug. 19, 1982 and between 9:30 and 10:00 A.M. on Mar. 2, 1983 under 150 foot-candle light intensity at Salinas, Calif. The color photograph shows the more golden bronze ray floret color.

CLASSIFICATION

Botanical: *Chrysanthemum morifolium,* Ramat., cv CHAMP.

Commercial: Disbud and spray decorative pot mum.

INFLORESCENCE

Capitulum:

*Form.*—Flat.

*Type.*—Decorative.

Diameter across face.—70 To 90 mm.

Corolla of ray florets:

*Color (general tonality from a distance of three meters).*—Summer: Golden Yellow. Winter: Golden Bronze.

*Color (abaxial).*—Summer 6A-B. Winter 14A-B.

*Color (adaxial).*—Summer 6C. Winter 14C.

*Shape.*—Oblong, rounded tip. Both flat and spoon.

Corolla of disc florets:

*Color (mature).*—13A.

*Color (immature).*—154C.

Reproductive organs:

*Androecium.*—Present disc florets only; scant pollen.

*Gynoecium.*—Present both ray and disc florets.

PLANT

General appearance:

*Height.*—Medium; 25 to 35 cm. given 2 long day weeks before pinch and lights out, and 1–2 applications of 2500 ppm B-9 SP after lights out

*Branching pattern.*—Prolific, spreading.

Foliage:

*Color (abaxial).*—147A.

*Color (adaxial).*—147B.

*Shape.*—Moderately lobed and very slightly serrated.

CHART A

COMPARISON OF CHAMP AND YELLOW MANDALAY

| CULTIVAR | RAY FLORET COLOR | CAPITULUM FORM AND TYPE | BRANCHING PATTERN |
|---|---|---|---|
| CHAMP | WINTER: GOLDEN BRONZE | FLAT, DECORATIVE | PROLIFIC SPREADING |
| | SUMMER: GOLDEN YELLOW | FLAT, DECORATIVE | PROLIFIC SPREADING |
| YELLOW MANDALAY | WINTER: YELLOW TINGED BRONZE | FLAT, DECORATIVE | PROLIFIC SPREADING |
| | SUMMER: YELLOW | FLAT, DECORATIVE | PROLIFIC SPREADING |

| CULTIVAR | DIAMETER ACROSS FACE OF CAPITULUM | PLANT HEIGHT | FLOWERING RESPONSES PERIOD |
|---|---|---|---|
| CHAMP | 70 to 90 mm. | MEDIUM | 9 WEEK |
| | 70 to 90 mm. | MEDIUM | 9+ WEEK |
| YELLOW MANDALAY | 75 to 100 mm. | SHORT | 9 WEEK |
| | 75 to 100 mm. | MEDIUM | 11 WEEK |

COMPARISONS MADE OF PLANTS GROWN AS PINCHED DISBUDDED POT MUMS IN SALINAS, CALIFORNIA AND LEAMINGTON, CANADA

I claim:

1. A new and distinct cultivar of *Chrysanthemum morifolium,* Ramat., named Champ as described and illustrated, and particularly characterized as to uniqueness by the combined characteristics of flat capitulum form; decorative capitulum type; golden yellow summer ray floret color; golden bronze winter ray floret color; diameter across face of capitulum ranging from 70 to 90 mm. at maturity; uniform nine week flowering response; medium plant height and spreading branching pattern that adapts equally well to pinched disbud or spray pot mum programs.

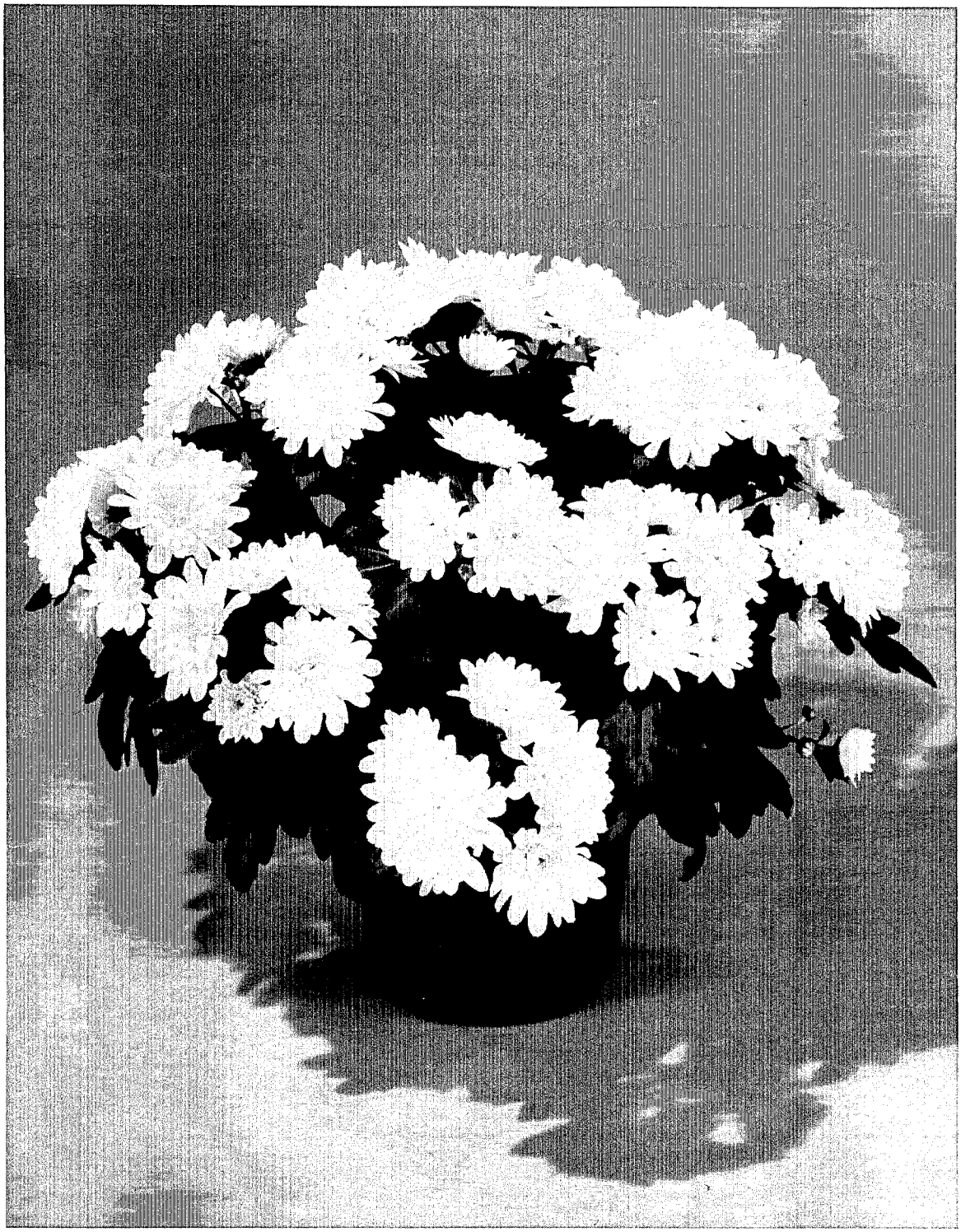

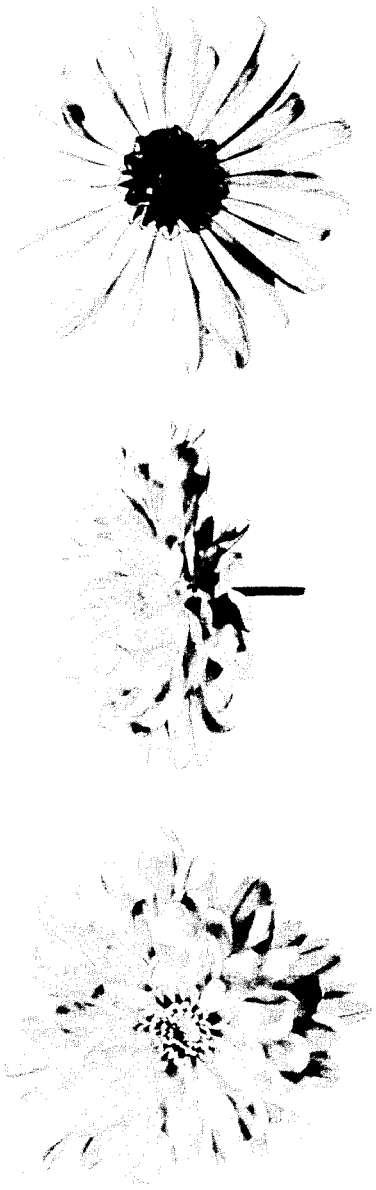

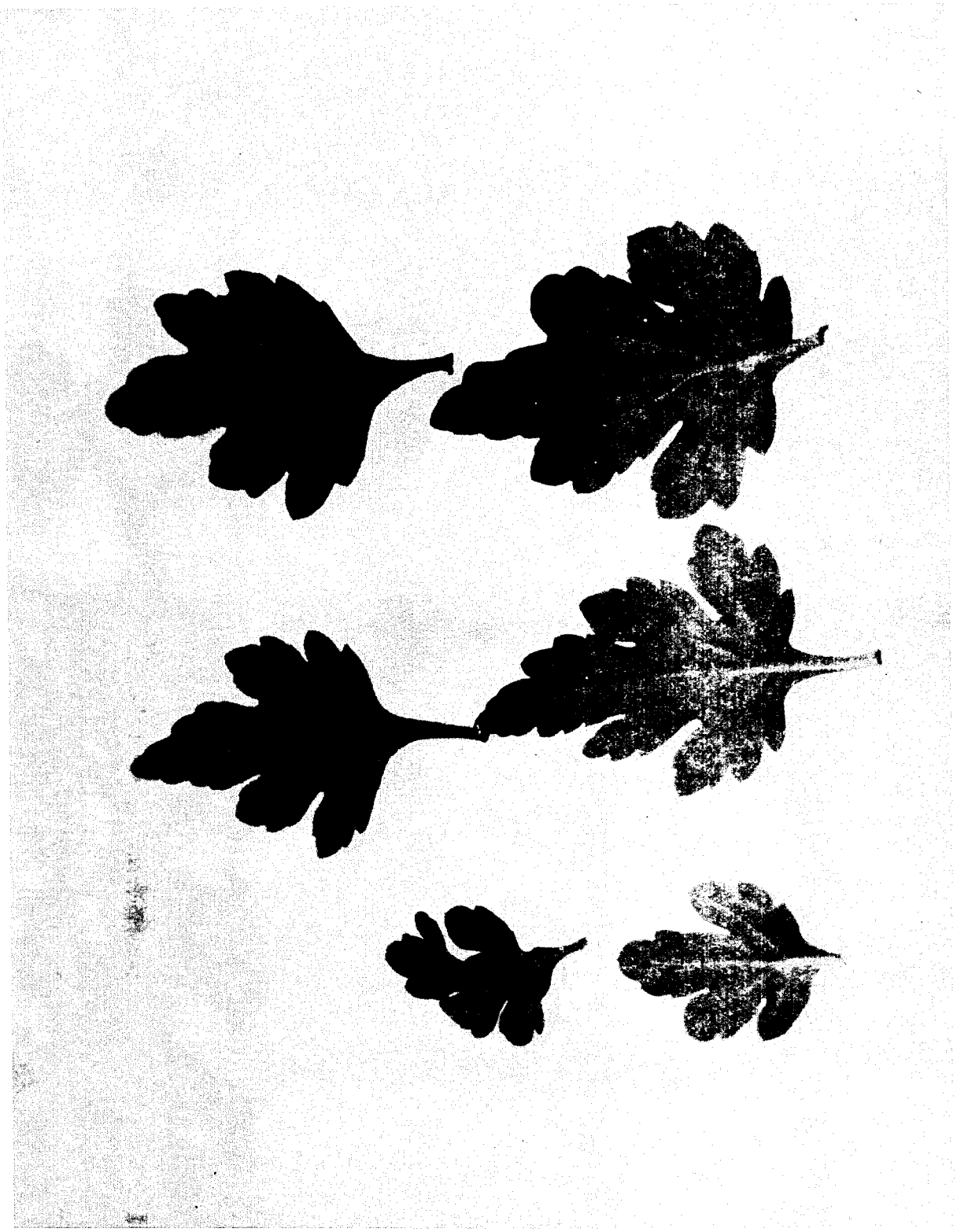

* * * * *